United States Patent [19]

Cernosek et al.

[11] Patent Number: 5,361,756
[45] Date of Patent: Nov. 8, 1994

[54] GUIDE AND CONTAINMENT MEMBER FOR LEADS FROM OPERATING ROOM MONITORING UNITS

[75] Inventors: Constance M. Cernosek, 1544 Prairie Grove Dr., Houston, Tex. 77077; Richard M. Blenderman, Houston, Tex.

[73] Assignee: Constance M. Cernosek, Houston, Tex.

[21] Appl. No.: 59,455

[22] Filed: May 7, 1993

[51] Int. Cl.$^5$ .......................... A61M 5/00; F16L 3/00
[52] U.S. Cl. ........................................ 128/630; 248/51
[58] Field of Search ................. 128/630; 248/51, 68.1, 248/70, 74.1, 74.4

[56] References Cited

U.S. PATENT DOCUMENTS

| | | | |
|---|---|---|---|
| 2,450,714 | 10/1948 | Campbell | 248/51 |
| 2,459,711 | 1/1949 | Meier | 248/68.1 |
| 2,715,002 | 8/1955 | Davis | 248/51 |
| 2,978,217 | 4/1961 | Gunderson | 248/51 |
| 3,312,434 | 4/1967 | Simon | 248/51 |
| 4,690,674 | 9/1987 | Dalglish | 248/51 |
| 5,102,399 | 4/1992 | Cho | 248/74.1 |

FOREIGN PATENT DOCUMENTS 2258512  2/1993  United Kingdom ................ 248/51

*Primary Examiner*—William E. Kamm
*Attorney, Agent, or Firm*—Pravel, Hewitt, Kimball & Kreiger

[57] ABSTRACT

A containment and guide arm for various leads extending from operating room monitoring devices such as a pulse oxygen metering unit and an EKG unit including a generally tubular member which is attachable to any stationary surface within the operating room or other such environment. A plurality of guide members are attached to the generally tubular member, each guide member including a plurality of guides or clamps for containing one or more leads extending from operating room monitoring devices thereby preventing the leads from being strewn about the operating room and hindering activity of doctors and nurses during operations. The containment and guide arm of this invention has similar application in other medical environments.

2 Claims, 3 Drawing Sheets

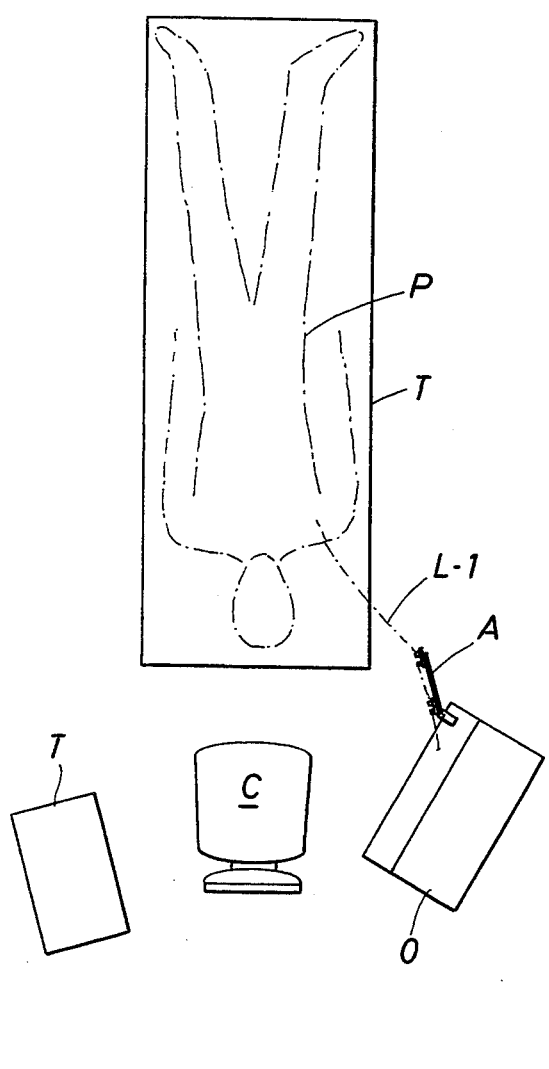
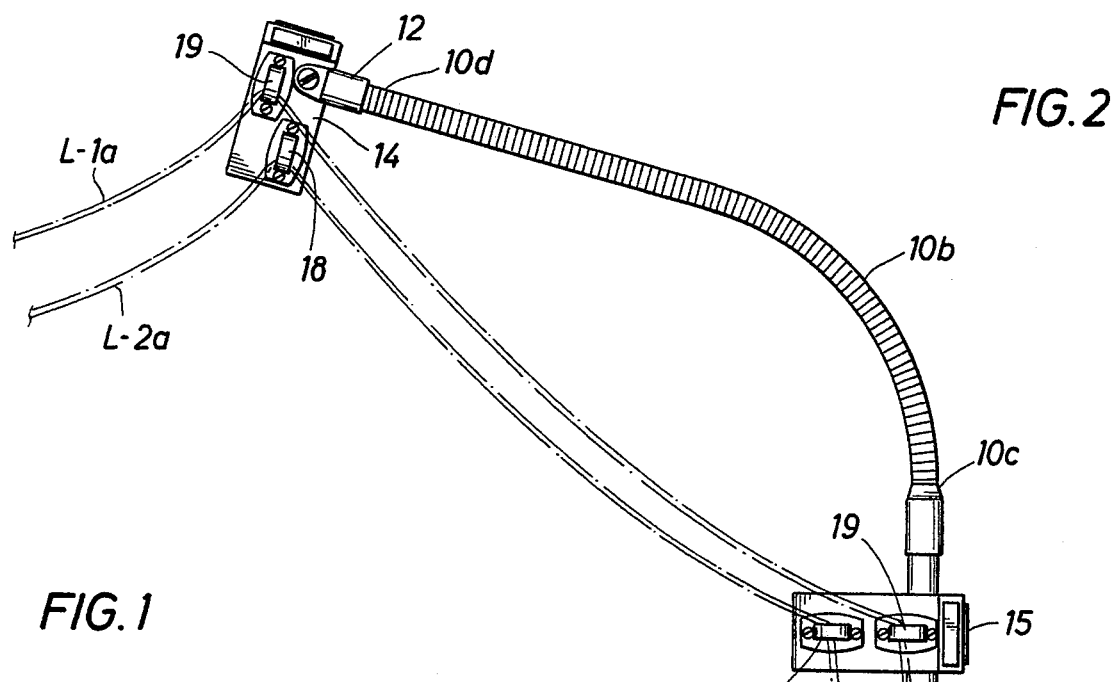

GUIDE AND CONTAINMENT MEMBER FOR LEADS FROM OPERATING ROOM MONITORING UNITS

FIELD OF THE INVENTION

The field of this invention relates to the containment of tubes and wire leads from monitoring equipment in operating rooms and other patient treatment environments.

BACKGROUND OF THE INVENTION

Typically, an anesthesiologist utilizes various patient vital signs monitoring equipment during an operation. Typical patient monitoring equipment includes a pulse oxygen meter as well as EKG, carbon dioxide, blood pressure, and temperature monitoring units. For each monitoring unit, a lead of some type extends from the monitoring unit to the patient. These leads may be electrical wires as in the case of the pulse oxygen meter, the EKG, and the temperature measurement unit or other tubing such as pneumatic tubing for the carbon dioxide and blood pressure monitoring units. Usually the distance between the monitoring devices and the location where the leads are connected to the patient, i.e., the operating table, is approximately 4-12 feet in length. These leads have no protective support, housing or defined path from the monitoring units to the patient. There is no set organized location for the units and thus the units and their leads are simply strung from the monitoring units to the patient just before the operation and rest on the floor or even in mid-air during the course of the operation. In many situations these connective leads are so haphazardly strewn about that they can hinder the anesthesiologist from concentrating upon the care of the patient thus creating an unnecessarily stressful situation. Such tubing can cause the operating room work space to become unworkable. The tubing can even become entangled under foot and obstruct ready access to the patient.

SUMMARY OF THE INVENTION

It is an object of this invention to provide a containment arm and guide for the various leads extending from operating room monitoring devices to the patient. The containment arm and guide of this invention is provided to contain and guide the various leads including but not limited to leads extending from pulse oxygen metering units, EKG units, and carbon dioxide, temperature and blood pressure monitoring units.

The containment arm and guide of this invention includes a generally tubular member and mount means attached to said generally tubular member for mounting the tubular member onto a stationary object such as the oxygen metering unit. The generally tubular member includes a bendable section. A plurality of lead guide assemblies are attached to the generally tubular member. Each of the lead guide assemblies have a plurality of guide segments or clamps for containing one or more leads extending from said operating room monitoring devices. Each of the guide assemblies includes an attachment mechanism for attaching the guide assembly anywhere along the length of the generally tubular member.

A free end retention unit is also provided for temporarily storing the free ends of the leads of the monitoring devices between operations. The free end retention unit includes an attachment mechanism for attaching said free end retention unit to the operating table or other stationary object such as the containment arm. A plurality of guide segments or clamps are mounted with the attachment mechanism for receiving and storing the free ends of the leads from the monitoring devices in between operations.

This description is only a summary of the invention and is not intended to define the actual scope of the patent claims as hereinafter set forth.

BRIEF DESCRIPTION OF THE DRAWINGS

FIG. 1 is a top, schematic view of the location and use of the containment and guide arm of the preferred embodiment of this invention in an operating room environment;

FIG. 2 is a side view of the containment and guide arm of the preferred embodiment of this invention;

DESCRIPTION OF THE PREFERRED EMBODIMENT

Figure 3:
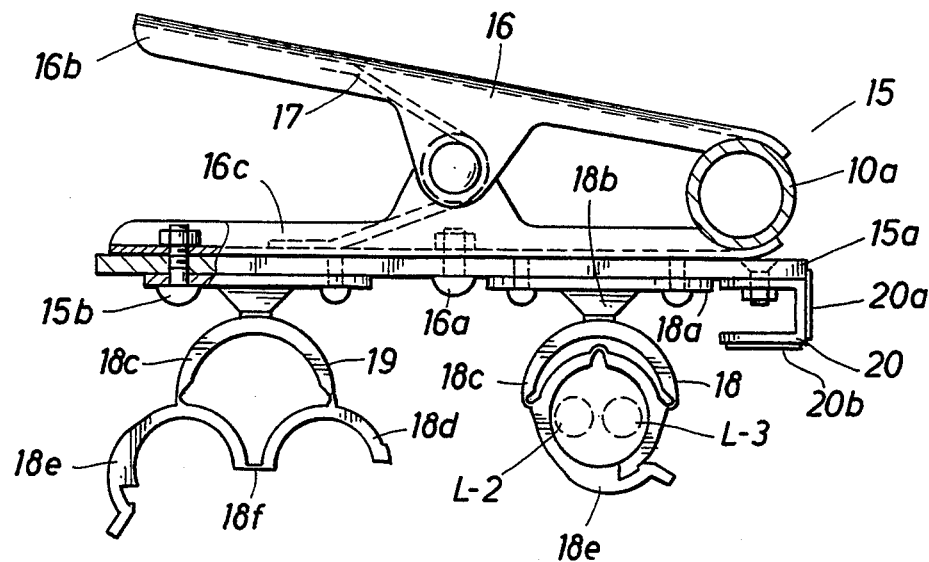
FIG. 3 is a side view, partly in section, taken along line 3—3 of FIG. 2 illustrating one of the lead guide units.

Referring to the drawings and in particular to FIG. 1, a patient P is illustrated on operating table T, which may be in an operating room, a clinic or other location. Typically, during an operation an anesthesiologist works from the chair C located near the head of the patient. On one side of the anesthesiologist and the chair C is a cart T for medicines. On the other side of the chair C and the anesthesiologist is an oxygen metering unit generally designated as O. The lead L-1 from the oxygen metering unit O is just one of a number of leads that extend from monitoring devices that are attached to the patient during operation. For example, the following is a chart of typical equipment, showing the size and nature of the lead, used as monitoring devices during operations:

| Unit | | Outer Diameter of Lead |
|---|---|---|
| 1. | pulse oximeter (electrical wire) | 3/32" |
| 2. | EKG (electrical wire) | 5/32"-3/16" |
| 3. | carbon dioxide (pneumatic tubing) | 1/16" |
| 4. | blood pressure (pneumatic tubing) | 1/4"-17/32" |
| 5. | temperature (electrical wire) | 1/8". |

Without this invention, these leads are strewn about the operating room and may get under foot during an operation or otherwise obstruct or hinder the ability of the doctors and nurses to move about the operating room. The containment and guide arm A of this invention is provided to contain and guide these various leads from monitoring devices to make the operating room safer and to allow doctors and nurses to move around more freely without obstruction during an operation.

The containment and guide arm A is further illustrated in the side view of FIG. 2. The containment and guide arm A includes a generally tubular housing 10 which includes a straight, rigid tubular section 10a and a bendable, tubular section 10b. It is anticipated that both the rigid section 10a and the bendable section 10b will be made of stainless steel but other suitable materials may be utilized. The rigid tubular member 10a is hollow and has a stainless steel coating on the outside. The rigid member 10a terminates in threaded connection with a coupling portion 11a which is welded or otherwise attached onto the mounting bracket or vice 11. The mounting vice 11 includes threaded screw member 11b for engaging almost any stationary structural member. For example, the containment and guide arm A can be attached to a flange or other edge formed with the housing of the oxygen metering unit O. The rigid tubular member 10a is attached to the bottom end 10c of the bendable portion of the tubular member 10 by threads or socket connection in a manner well-known in the art.

The bendable section 10b is also made of stainless steel but is coiled in a well-known manner to produce a longitudinal portion that is bendable to various positions. The upper or outer end 10d of the bendable section terminates in a coupling 12 which has a U-shaped end (not shown) for receiving the base of the guide unit 14. Lead guide units 15 (two in number) are mounted onto the tubular member 10 at various positions in order to support, guide and contain multiple leads.

Figure 4:
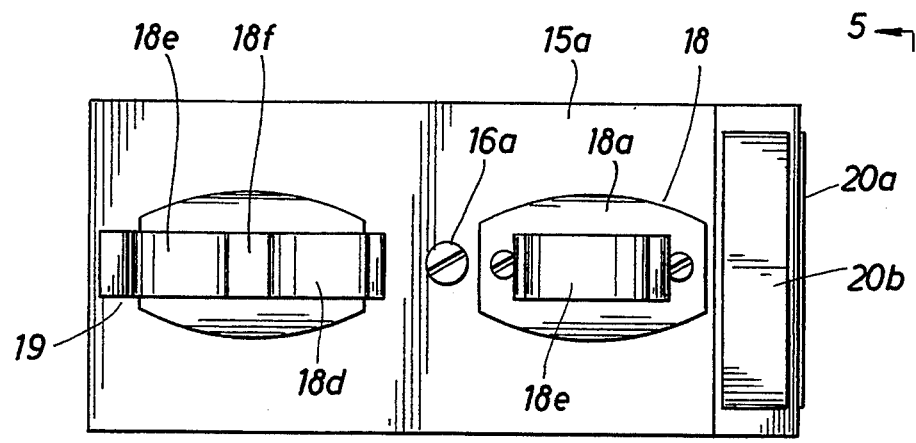
FIG. 4 is a bottom view of the guide unit of FIG. 3.
Figure 5:
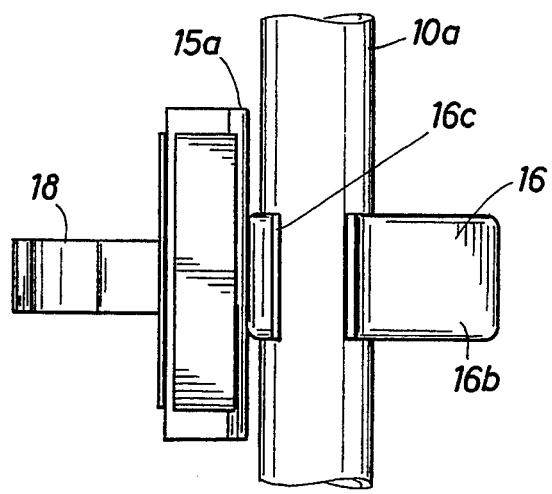
FIG. 5 is an end view of the guide unit of FIG. 4 as viewed from line 5—5 of FIG. 4.

Referring now to FIGS. 3–5, the lead guide unit 15 will be described in detail. The guide unit 15 includes a flat, base plate 15a. A spring-biased attachment clip 16 is attached by means of a nut and bolt combination 16a to the base plate 15a. The clip 16 is of a well-known commercial variety and includes two clipping or clamping members 16b and 16c which were interconnected for pivotal movement and spring-biased to a closed position by spring 17. The spring-biased clip member 16 may be coated with a plastic sheath so that the clip may be easily cleaned as necessary.

Two guide segments or clamps 18 and 19 are mounted onto the other side of the base plate 15a by a series of nut and bolt members such as 15b. The guide members 18 and 19 are molded from a suitable polymeric material. Since the guides 18 and 19 are identical, the same numbers and elements will be used to describe the same parts. In FIG. 3, the guide member 18 is illustrated in the closed position which may contain one or more leads such as L-2 and L-3 which extend from two of the monitoring units to the patient. The guide members 18 and 19 each include a base 18a which is attached by nuts and bolts such as 18b to the guide base 15a. The base includes a central support 18b which supports a semicircular support portion 18c. The semicircular support portion 18c supports on one side semicircular closure member 18d and on the other side semicircular closure member 18e. These members are integrally, pivotally attached to each other by a narrow portion of material at 18f so that the semicircular closure members may be rotated toward each other into a clipped or clamped, closed position in order to contain leads such as L-2 and L-3. The guide sections or segments 18 and 19 are only one of a number of types of such lead guides which may be utilized. U-shaped channel 20 is mounted onto one end of the plate member 15a by suitable nuts and bolts and includes first and second name plates 20a and 20b.

Referring now to FIG. 2, the movable guide units 15 are mountable onto either the rigid elongated member 10a or onto the bendable portion 10b of the elongated member 10 at any locations. While two of the guide units 15 are illustrated in FIG. 2, it should be understood that more guide units may be utilized if necessary.

The guide unit 14 is permanently attached to the coupling 12 by means of suitable screws. The guide unit 14 does not have a spring-biased clip 16. The guide unit 14 is otherwise identical to the guide units 15.

Thus as illustrated in FIG. 2, leads such as L-1 and L-2 as well as other leads not shown are contained within the circular clamps 18 and 19 of the moveable guide units 15. The leads such as L-1 and L-2 are also clamped in semicircular clamps 18 and 19 in the guide unit 14 affixed to the top end of 10d the bendable segment 10b. In this manner, the leads such as L-1 and L-2 are held off of the ground and are maintained in general alignment with the elongated member 10 so that the leads are confined to a specific area thus minimizing the potential for hindering movements of the doctors and nurses during surgery.

Figure 7:
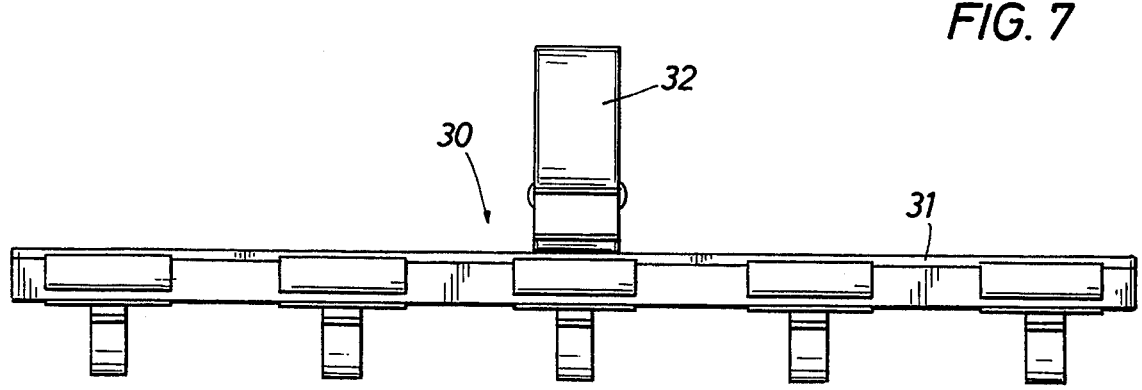
FIG. 7 is a top view of the free end retention unit of this invention.
Figure 6:
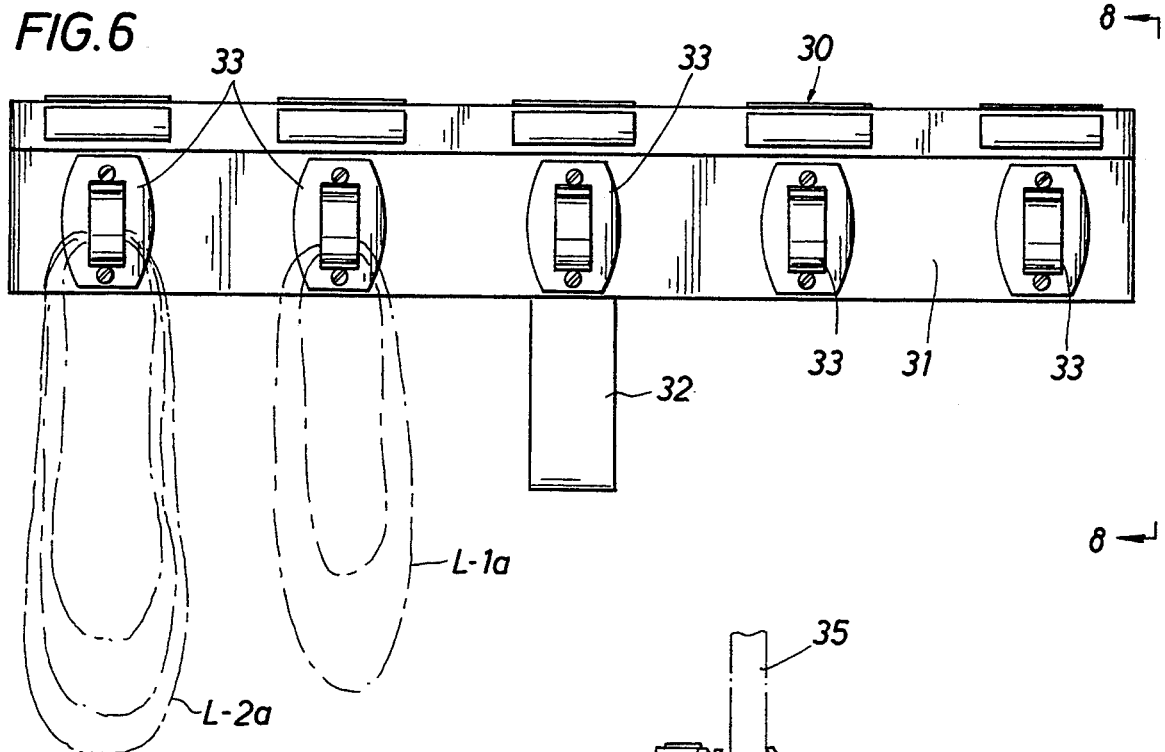
FIG. 6 is a side view of the free end retention unit of this invention.
Figure 8:
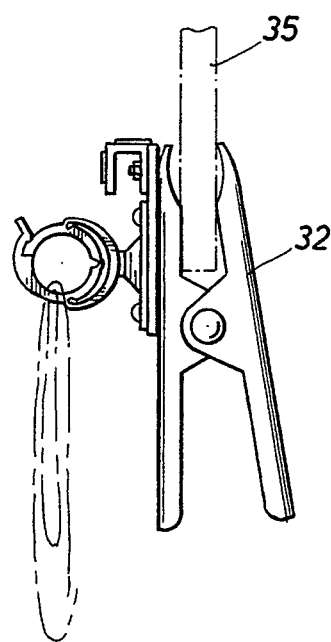
FIG. 8 is an end view of the free end retention unit of this invention from the view of line 8—8 of FIG. 6.

At the end of surgery, it is necessary to temporarily store the free ends L-1a and L-2a of the leads L-1 and L-2 (as well as the free ends of any 30 other leads which are confined within the guide units 14 and 15). The leads L-1a and L-2a extend from monitoring equipment through guide arm A into attachment with the patient during an operation. At the end of the operation, these leads, which may be several feet to 6 feet or more in length, must be stored until the next operation. Referring to FIGS. 6–8, the free ends of leads such as L-1a and L-2a are temporarily stored in the free end retention unit generally designated by the number 30 in FIGS. 6–8.

The free end retention unit 30 includes a generally rectangular base plate 31 having a spring-biased clip 32 attached by suitable nut and bolt assemblies to the rear side of the base plate 31. The spring-biased clip 32 is identical to the spring-biased clip 16 of the guide units 15 and thus need not be further described. A plurality of circular clamps 33 are mounted onto the front surface of the base plate 31 at equally spaced intervals from each other. Each of the clamps 33 are identical to either of the clamps 18 and 19 and thus need not be further described. With the clamps in the open position such as illustrated for clamp 19 in FIG. 3, the free ends L-2a, L-1a as well as the free ends of any other leads may be coiled onto the open interior of the semicircular clamps, which are then closed such that the clamps 33 hold several rounds of coils of the free ends of the leads. The entire retainer unit or storage unit 30 may be attached to an edge 35 of the operating table O or to any other edge to temporarily hold the coiled, free ends such as L-1a and L-2a of the leads L-1 and L-2. The retention or storage unit 30 can be clamped to a stationary member such as the hospital table edge 35 or even the arm 10 before or after the free ends of the leads are coiled about the circular clamps 33. The retention units 30 temporarily store the free ends of the leads between operations such that the leads do not get soiled or otherwise hinder activity within the operating room between operations.

Having described the invention above, various modifications of the techniques, procedures, material and equipment will be apparent to those in the art. It is intended that all such variations within the scope and spirit of the appended claims be included under the doctrine of equivalence. For example, while the clamps 18, 19, and 33 have been described herein to hold the leads such as L-1 and L-2, it should be understood that other suitable clamps may be utilized. The spring-biased clips which mount the movable guide units 15 and the storage unit 33 may also be replaced by another form of attachment mechanism if desired. It is within the scope of this invention to vary the number of the movable guide units 15. It is also within the scope of this invention to vary the number of circular clamps 18 and 19 that are utilized with each of the movable guide members 15. It is within the scope of this invention further to vary the number of semicircular clamps 33 used with the temporary lead storage unit or retainer unit 30. These and other variations may be made within the scope of this invention.

We claim:

1. A containment and guide arm for various leads extending from operating room monitoring devices such as a pulse oxygen metering unit, EKG unit, carbon dioxide, temperature and blood pressure monitors, comprising:

a tubular member, mount means for attachment to said tubular member for mounting said tubular member onto a stationary object;

said tubular member including a bendable section, said bendable section of said tubular member terminating in an outer end;

a plurality of guide assemblies, each of said guide assemblies including means for attachment of said guide assembly to said tubular member anywhere along the length of said tubular member;

each of said guide assemblies having a plurality of guide segments for containing at least one of such operating room leads extending from said monitoring devices to a patient;

said guide segments including first and second containment members being movable between open and closed positions, said first and second containment members forming a contained area in order to receive at least one lead with said first and second containment members in said open position and for containing said at least one lead with said first and second containment members in said closed position;

each of said guide assemblies including attachment means for attaching each of said guide assemblies anywhere along the length of said tubular member, said attachment means being a pivotal clip, said clip including first and second clip members pivotally attached to each other, said first and second clip members having a spring mounted therewith in order to bias said clip members to a closed position for mounting of said guide assemblies anywhere along the length of said tubular member; and one of said guide assemblies being attached to said outer end of said tubular member.

2. The containment and guide arm of claim 1, including:

a free end retention unit including means for temporarily storing free ends of said leads, said free end retention unit including an means for attaching said free end retention unit to a table;

a plurality of guide members mounted with said free end retention unit and including means for receiving and storing said free ends of said leads in a coiled form.

* * * * *